United States Patent [19]

Kleemann et al.

[11] Patent Number: 4,827,029

[45] Date of Patent: May 2, 1989

[54] PROCESS FOR THE ISOLATION OF L-AMINO ACIDS

[75] Inventors: Axel Kleemann, Muehlheim; Kurt Klostermann, Goldbach; Wolfgang Leuchtenberger, Bruchkoebel, all of Fed. Rep. of Germany; Rudi E. Moerck, Montville, N.J.; Michael Karrenbauer, Moos-Bankholzen, Fed. Rep. of Germany

[73] Assignee: Degussa Aktiengesellschaft, Frankfurt am Main, Fed. Rep. of Germany

[21] Appl. No.: 146,637

[22] Filed: Jan. 21, 1988

[30] Foreign Application Priority Data

Jan. 30, 1987 [DE] Fed. Rep. of Germany ....... 3702689

[51] Int. Cl.$^4$ .............................................. C07C 99/12
[52] U.S. Cl. ...................................... 562/559; 562/575
[58] Field of Search ............... 562/443, 444, 559, 575, 562/402

[56] References Cited

U.S. PATENT DOCUMENTS

| | | | |
|---|---|---|---|
| 2,949,450 | 8/1960 | Stark | 562/459 |
| 4,133,753 | 1/1979 | Takeuchi et al. | 562/443 |
| 4,496,703 | 1/1985 | Steinmetzer | 562/443 |
| 4,584,399 | 4/1986 | Portal et al. | 562/443 |
| 4,661,629 | 4/1987 | Valus et al. | 562/443 |

FOREIGN PATENT DOCUMENTS

| | | | |
|---|---|---|---|
| 2008842 | 11/1970 | Fed. Rep. of Germany | 562/402 |
| 51-138603 | 11/1976 | Japan | 562/402 |

*Primary Examiner*—James H. Reamer
*Attorney, Agent, or Firm*—Beveridge, DeGrandi & Weilacher

[57] ABSTRACT

L-amino acids present in cleavage solutions obtained in the acylase-catalyzed cleavage of N-acetyl-D,L-amino acids are isolated by use of a strongly acidic ion exchanger in H+ form. First, the mother liquor from a previous treatment cycle is fed to the ion exchanger, and then the cleavage solution and finally the wash water and the discharge from the ion exchanger which is pH-controlled is analyzed into an "effluent water fraction", an "N-acetyl-D-amino acid fraction" and an "L-amino acid fraction". The last fraction is adjusted by addition of fresh cleavage solution to a pH of between 4.0 and 6.0, and from the mixture which is thus obtained the L-amino acid is isolated by crystallization. The mother liquor which is obtained is recycled back into a subsequent treatment cycle.

6 Claims, No Drawings

PROCESS FOR THE ISOLATION OF L-AMINO ACIDS

INTRODUCTION AND BACKGROUND

The present invention relates to a process for the isolation of L-amino acids from the cleavage solution produced as a result of the acylase-catalyzed cleavage reaction of N-acetyl-D,L-amino acids using a strongly acidic ion exchanger in the H+ form.

The essential principle of the acylase-catalyzed cleavage reaction of N-acetyl-D,L-amino acids into L-amino acid, acetic acid and N-acetyl-D-amino acid are known in the art. The cleavage reaction is traditionally undertaken in a solution of the N-acetyl-D,L-amino acid which is between a 0.4 and a 1.0 molar solution and at a pH of between 6 and 8. The N-acetyl-D,L-amino acid is customarily used in the form of the sodium or potassium salt.

It is also known in the art to isolate the L-amino acid from the cleavage solution by evaporation and final cooling down to crystalline form. The drawback of this direct treatment of the crude cleavage solution resides in the fact that sodium or potassium acetate salts are also precipitated, together with the L-amino acid, and this contaminates the L-amino acid.

Following the separation of the crystallized L-amino acid, the mother liquor remaining is processed by commercially known effluent technology processes for recovery of N-acetyl-D,L-amino acid. With the direct processing of the crude cleavage solution, the mother liquor also contains among other things considerable quantities of the L-amino acid. If this mother liquor is to be processed into N-acetyl-D,L-amino acid, as a first step, the L-amino acid which is contained therein must be newly acetylated, because otherwise peptides are formed during the re-racemization of the N-acetyl-D-amino acid. This means that the L-amino acid which has been released by acylase must be subjected again, after acetylization and re-racemization, to another acylase-catalyzed cleavage. Thus, the necessary quantity of acylase is increased and an additional product loss occurs with the re-racemization.

Finally, it is also known to isolate the L-amino acid which is contained in the crude cleavage solution with use of a strongly acidic ion exchanger in the H+ form. In that process, a sufficient quantity of cleavage solution is fed to the ion exchanger so that the ion exchange material is loaded up to 80 to 85% of its capacity with alkali metal ions and L-amino acid molecules. Following washing out with water, the L-amino acid is eluted from the ion exchanger with an aqueous ammonia solution. As a result of the evaporation and subsequent cooling down, the L-amino acid is obtained from the eluate in crystalline form. If an approximately 3N ammonia solution is used for the elution, alkali metal ions are also partially obtained in the eluate and these ions lead to an increased ash content in the crystallized L-amino acid product. This drawback can now actually be overcome to a great extent by use of a diluted ammonia solution, for instance an 0.4 or 0.5N solution. Then, however, a very diluted eluate is obtained, which requires an extended evaporation time, which then again leads to increased by-product formation and/or racemization of the L-amino acid. Another drawback of this known process resides in that the ion exchanger can only be used up to approximately 45 to 50% of its capacity for the bonding of alkali metal ions.

SUMMARY OF THE INVENTION

In accordance with the process of the present invention, a process for the isolation of L-amino acids is carried out using the cleavage solution produced as a result of the acylase-catalyzed cleavage reaction of N-acetyl-D,L-amino acids using a strongly acidic ion exchanger in the H+ form. The ion exchanger is operated at a temperature of between 30° and 90° C., and a selected sequence of process steps is followed: In the first step in the sequence, the mother liquor from a previous isolation treatment cycle is fed onto the ion exchanger, followed by the cleavage solution and finally the wash water. The discharge liquid from the ion exchanger is pH-controlled, is analyzed and diverted in three fractions, of which the first fraction extends from the beginning of the treatment process until a pH of 2.0 is reached, the second fraction extends from an initial pH 2.0 until after a pH of 2.0 is again reached following a drop in pH to less than 2 after which it again rises to 2; and the third fraction of which extends from the end of the second fraction cleavage until the discharge run off reaches a pH of 5.0. The third fraction as described is combined with the discharge being obtained during the feed of the wash water. This mixture is then adjusted by addition of fresh cleavage solution to a pH of between 4.0 and 6.0. The L-amino acid contained therein is isolated from the adjusted mixture in a known manner, and that the mother liquor thereby obtained is recycled into a subsequent isolation treatment cycle.

DETAILED DESCRIPTION OF THE INVENTION

The process according to the present invention is especially suitable for the treatment of the cleavage solutions obtained from N-acetyl-D,L-methionine, N-acetyl-D,L-valine and N-acetyl-D,L-phenylalanine.

Ion exchangers suitable for purposes of the invention are for instance the commercially available products based on products made up of divinyl benzene cross-linked sulfonated polystyrene.

The ion exchanger is preferably operated at a temperature of between 60° and 80° C.

As an initial step in the reaction sequence of the present invention, first the mother liquor obtained from the L-amino acid crystallization of a previous isolation treatment cycle, and then the fresh cleavage solution, which has a pH of between 6.0 and 8.0, are fed to the ion exchanger. Both solutions are preferably preheated to the desired temperature. When the process of the invention is carried out for the very first time and no mother liquor is yet present from a previous isolation treatment cycle, then the process is begun with fresh cleavage solution.

The discharge from the ion exchanger is begun as a first fraction ("effluent water fraction") and continued until the pH of the discharge decreases to 2.0. This fraction is discarded. Then, the recipient vessel is switched and the subsequent discharge is begun as a second fraction ("acetyl fraction") until the pH of the discharge, after it first drops still further, rises again to 2.0. This fraction, with a pH lower than 2.0, contains mainly the free N-acetyl-D-amino acid and acetic acid and is therefore fed to the re-racemization.

The recipient vessel is switched again and the subsequent discharge is begun as the third fraction ("L-amino acid fraction"). During the feed of the mother liquor and the cleavage solution, the ion exchanger is charged with alkali metal ions and L-amino acid molecules.

As a result of the different degrees of basicity of the alkali metal ions and the L-amino acid molecules, the alkali metal ions are more strongly bonded to the ion exchanger than the L-amino acid molecules. Subsequently arriving alkali metal ions therefore penetrate in the feed area of the ion exchanger into already bonded L-amino acid molecules in the direction of the discharge area, where they are bonded again. In the ion exchange columns then, after some time in the feed area, only alkali metal ions are still bonded, and in the discharge area only L-amino acid molecules are still bonded. With the feed of additional cleavage solution, then, the L-amino acid molecules which were bonded in the ion exchange columns are also forced into the discharge, which also contains other remaining N-acetyl-D-amino acid and acetic acid. The feed of cleavage solution is then terminated when the pH in the discharge has risen to 5.0.

The ion exchanger is now washed and rinsed with water until all dissolved materials hae been removed from the discharge. If desired, the wash water is likewise preheated to the desired operational temperature of the ion exchanger. The discharge being obtained with the washing or rinsing is combined with the "L-amino acid fraction".

The ion exchanger is now practically completely charged with alkali metal ions. Maximum utilization of its capacity is thus attained. It can be regenerated in a known manner with a diluted acid, for instance with aqueous sulfuric acid. L-amino acid can no longer be detected in the run off of the regeneration.

The mixture made up of the "L-amino acid fraction" and the discharge occurring with washing and rinsing of the ion exchanger has a pH of between 2.5 and 3.5. If this mixture is then directly evaporated and cooled, for the purpose of crystallization, then the resulting L-amino acid obtained thereby is strongly contaminated with N-acetyl-D-amino acid. It is therefore first replaced with a sufficient quantity of fresh cleavage solution so that a pH of between 4.0 and 6.0, preferably of between 4.5 and 5.5 is obtained. Then, this solution is placed under decreased pressure and evaporated from approximately 20% to approximately 50% of the original volume and is cooled down for the purpose of crystallization, and an L-amino acid is obtained which is nearly free of N-acetyl-D-amino acid and has a specifically calculated ash proportion and specific degree of rotation.

The isolation yield of L-amino acid generally lies in the range of between 40 and 80% of the total of L-amino acid which is used, including that in the form of mother liquor and that in the form of fresh cleavage solution. If the mother liquor remaining with the L-amino acid crystallization were to be returned into the re-racemization and then to renewed racematization cleavage, then this would give rise to unavoidable production losses. However, since the mother liquor is carried back from recycle into a subsequent treatment cycle, no product losses occur, but rather the yield of isolation of L-amino acid is enhanced by the continuous return and reuse of over 95% of the mother liquor.

The invention is further described by the following examples:

EXAMPLE 1

This example illustrates carrying out the process according to the invention, when there is not yet any mother liquor present from a previous treatment cycle, using a cleavage solution of N-acetyl-D,L-methionine:

An ion exchanger column was used, filled with 1.5 liters of a strongly acidic ion exchanger (Duolite C 26 ®) in the H+ form, which was preheated to 70° C. by means of hot water.

A cleavage solution of the following composition was treated:
38.5 g/l L-methionine
66.3 g/l N-acetyl-D-methionine and
14 g/l sodium ions.

This cleavage solution was placed in the prepared ion exchanger at a temperature of 70° C. and at a flow velocity of 3.5 l/hour, until the pH had dropped to 2.0 in the discharge. Then the recipient vessel was changed and the first discharge fraction ("effluent water fraction") which was obtained in a quantity of 1.2 liters was discarded.

With further feeding of the cleavage solution, the pH in the discharge dropped below 2.0 and then rose again. When the pH reached 2.0 once again, the recipient vessel was changed again. The second discharge fraction ("acetyl fraction") which was obtained in a quantity of 2.0 liters can be fed into the re-racemization.

With further feeding of the cleavage solution, the pH in the discharge again rose and the feeding was continued until a pH of 5.0 was attained. This occurred after the feeding of a total of 4.8 liters of cleavage solution. Then the ion exchanger was washed out with 2.0 liters of water at 70° C. Included in the washing water, a third discharge fraction ("L-methionine fraction") was obtained in quantity of 3.6 liters and of the following composition:
50 g/l L-methionine,
51 g/l N-acetyl-D-methionine and
7.7 g/l sodium ions.

This "L-methionine fraction" was then mixed thoroughly with 3.0 liters of fresh cleavage solution of the aforementioned composition. The mixture with a pH of 5.0 was evaporated at reduced pressure at a temperature of 70° C., until L-methionine began to be precipitated. Then, the suspension was heated to 80° C. and an activated charcoal settling and clarification was carried out.

The clear filtrate was cooled down to 20° C. within 7 hours. The L-methionine which was crystallized out was filtered and dried.

Yield: 135 grams (=45% of the total L-methionine contained in the cleavage solution which was used).

| Results of analysis: | |
| --- | --- |
| Percentage/proportion: | 99.7% |
| Ash Percentage/proportion: | 0.02% |
| Transmission: | 98.5% |
| $[\alpha]_D^{20} = +25.5°$ | |

The remaining mother liquor had the following composition:
46 g/l L-methionine,
98 g/l N-acetyl-D-methionine and
20 g/l sodium ions.

The mother liquor is fed to the subsequently following treatment cycle.

The ion exchanger column was charged from above with 3 liters of an 8% by weight sulfuric acid solution, was back-purged, and washed sulfate-free with water. It is then prepared for reuse.

EXAMPLE 2

This example shows a complete treatment cycle by the process according to the invention with use of the mother liquor which was obtained from Example 1.

The ion exchanger column and the cleavage solution of Example 1 were used and the procedure was again carried out at the temperatures of Example 1.

To begin with, 3 liters of mother liquor heated to 70° C. were removed from Example 1 and placed in the ion exchanger, along with 1.3 liters of cleavage solution heated to 70° C., and it was post-washed with 2.2 liters of water at 70° C. The changing of the recipient vessel was undertaken in this case when the pH level indicated in Example 1 was reached. The following fractions were obtained:
1. 700 ml of "effluent water fraction"
2. 2.1 liters of "acetyl fraction"
3. 3.7 liters of "L-methionine fraction" with
    50 g/l L-methionine and
    55 g/l N-acetyl-D-methionine, and
    9.5 g/l sodium ions.

The "L-methionine fraction" was processed as in Example 1. The L-methionine yield was 118 grams (=40%).

| Results of analysis: | |
|---|---|
| Percentage content: | 99.8% |
| Ash Percentage: | 0.02% |
| Transmission: | 98% |
| $[\alpha]_D^{20} = +24.1°$ | |

In relation to the total volume of cleavage solution used in Examples 1 and 2, the isolation yield was 54% L-methionine. With reference to the L-methionine which is found in the mother liquor of Example 2, and which can be isolated in the subsequent processing cycles, the total yield of crystallized L-methionine is 95%.

EXAMPLE 3

An ion exchanger column filled with 30 liters of a strongly acidic ion exchanger (Duolite C 26 ®) in the H+ form, which was preheated to 70° C. by means of hot water.

63 liters of mother liquor from a previous L-methionine crystallization, heated to 70° C., was fed to the ion exchanger with a flow velocity of 70 liters/hour, and with the following composition
36.8 g/l L-methionine,
110.5 g/l N-acetyl-D-methionine and
19.8 g/l sodium ions,
including 21 liters of cleavage solution heated to 70° C., with
37.0 g/l L-methionine
67.4 g/l N-acetyl-D-methionine and
14.6 g/l sodium ions
and the mixture was post-washed with 40 liters of water warmed to 70° C.

The recipient vessel was changed once again when the pH levels were reached as indicated in Example 1.
The following fractions were obtained:
1. 19 liters of "effluent water fraction"
2. 42 liters of "acetyl fraction"
3. 63 liters of "L-methionine fraction" with
    47.7 g/l L-methionine
    60.2 g/l N-acetyl-D-methionine and
    7.5 g/l sodium ions.

The processing of the "L-methionine fraction" occurred as in Example 1 with addition of 57 liters of fresh cleavage solution of the same composition as above.

| Results of analysis: | |
|---|---|
| Percentage content: | 99.8% |
| Ash Percentage/content: | 0.05% |
| Transmission: | 98% |
| $[\alpha]_D^{20} = +24.3°$ | |

EXAMPLE 4

The ion exchanger column of Example 3 was used and mother liquor, cleavage solution and water for the post-washing were all used again, preheated to 70° C.

First of all, 74 liters of mother liquor from a previous L-methionine crystallization and with the following composition were fed to the ion exchanger.
41.8 g/l L-methionine
119.8 g/l N-acetyl-D-methionine and
20.8 g/l sodium ions.
and then 10 liters of cleavage solution, with
35.7 g/l L-methionine
70.0 g/l N-acetyl-D-methionine and
14.2 g/l sodium ions
and it was post-washed with 40 liters of water.

The recipient vessel was changed in this case when the pH value was reached as indicated in Example 1.
1. 14 liters of "effluent water fraction"
2. 47 liters of "acetyl fraction"
3. 63 liters of "L-methionine fraction" with
    54.3 g/l L-methionine 70.0 g/l N-acetyl-D-methionine and 7.0 g/l sodium ions.

The processing of the "L-methionine fraction" occurred as in Example 1 with addition of 78.5 liters of fresh cleavage solution of the composition described above.

The L-methionine yield was 2501 grams (40% of theory).

| Results of analysis: | |
|---|---|
| Percentage/content: | 98.5% |
| Ash Percentage/content: | 0.3% |
| Transmission: | 97.5% |
| $[\alpha]_D^{20} = +24.1°$ | |

EXAMPLE 5

An ion exchanger column was used, filled with 940 ml of a strongly acidic ion exchanger (Duolite C 26 ®) in the H+ form, which was preheated to 70° C. by means of hot water.

First of all, 990 ml of the mother liquor from a previous L-valine crystallization were fed to this column, with the following composition:
24.2 g/l L-valine
191 g/l N-acetyl-D-valine and
7.8 g/l sodium ions, which was heated to 70° C., and it included 100 ml cleavage solution heated to 70° C., with 31.8 g/l L-valine
51.6 g/l N-acetyl-D-valine and
13.8 g/l sodium ions and it was post-washed with 300 ml volume of water at 70° C. The change of the recipient vessel was undertaken in this case when the pH value indicated in Example 1 was attained. The following fractions were obtained.

1. 650 ml of "effluent water fraction"
2. 840 ml of "acetyl fraction"
3. 900 ml "L-valine fraction" with
   30 g/l L-valine
   61 g/l N-acetyl-D-valine and
   3.1 g/l sodium ions.

The processing of the "L-valine fraction" occurred similarly as in Example 1 with addition of 1.8 liters of fresh cleavage solution of the composition described above. The yield of L-valine was 97 grams with a percentage/content of greater than 99%. This corresponds to an isolation yield of 83%.

| Results of analysis: | |
|---|---|
| Ash Percentage/content | 0.0% |
| Transmission: | 95.7% |
| $[\alpha]_D^{20}$ +28.1° | |

Further variations and modifications of the foregoing will be apparent to those skilled in the art from a reading thereof and are intended to be encompassed by the claims appended hereto.

The German priority application No. P 37 02 689.5-42 is relied on and incorporated herein by reference.

We claim:

1. A process for the isolation of L-amino acids from the cleavage solutions obtained in the acylase-catalyzed cleavage of N-acetyl-D,L-amino acids in the presence of a strongly acidic ion exchanger in the H+ form, comprising: charging an ion exchanger column maintained at a temperature of between 30° and 90° C., with cleavage solution obtained from the cleavage of N-acetyl-D,L-amino acids, contacting said ion exchanger with wash water, separating the discharge from the ion exchanger under pH control into three fractions, of which the first fraction extends from the beginning of the treatment process until the pH of 2.0 is reached, and of which the second fraction extends from pH 2.0 until the pH after falling below 2 rises back to 2.0 again, and of which the third fraction extends from the point terminating the second fraction during the feed of the cleavage solution until a pH of 5.0 is reached, combining said third fraction with the discharge being obtained during the feed of the wash water and adding thereto fresh cleavage solution to adjust the pH of the mixture of between 4.0 to 6.0, isolating the L-amino acid from the said adjusted mixture by crystallization, and recycling the mother liquor which is thus obtained back into a subsequent treatment cycle.

2. The process according to claim 1 wherein the ion exchanger is operated at a temperature of between 60° and 80° C.

3. A process according to claim 1 wherein the mixture of the third fraction with the discharge being obtained during the feed of the wash water by addition of fresh cleavage solution is set at a pH of between 4.5 and 5.5.

4. A process for the isolation of L-amino acids from the cleavage solutions accumulating during the acylase-catalyzed cleavage of N-acetyl-D,L-amino acids in the presence of a strongly acidic ion exchanger in the H+ form, comprising:

carrying out an ion exchange at a temperature of between 30° and 90° C., in a first step by contacting mother liquor having been obtained from a previous treatment cycle with said ion exchanger, in a second step contacting said ion exchanger with cleavage solution obtained in said cleavage of N-acetyl-D,L-amino acids, and in a third step contacting said ion exchanger with washing water, separating the discharge from the ion exchanger under pH control into three fractions, of which the first fraction extends from the beginning of the reaction until the pH of 2.0 is reached, and of which the second fraction extends from pH 2.0 until the pH after falling below 2 then rises to 2.0 again, and of which the third fraction extends from the point terminating the second fraction during the feed of the cleavage solution until a pH of 5.0 is reached, combining said adjusted third fraction with the discharge being obtained during the feed of the wash water and adding thereto fresh cleavage solution to adjust the pH of the mixture to a value between 4.0 to 6.0, isolating the L-amino acid from the said mixture by crystallization, and recycling the mother liquor which is thus obtained back into a subsequent treatment cycle.

5. The process according to claim 4 wherein the ion exchanger is operated at a temperature of between 60° and 80° C.

6. A process according to claim 4 wherein the mixture of the third fraction with the discharge being obtained during the feed of the wash water by addition of fresh cleavage solution is set at a pH of between 4.5 and 5.5.

* * * * *